(12) United States Patent
He et al.

(10) Patent No.: US 6,582,441 B1
(45) Date of Patent: Jun. 24, 2003

(54) SURGICAL INSERTION TOOL

(75) Inventors: Tom Xiaohai He, Simi Valley, CA (US); James P. McGivern, Stevenson Ranch, CA (US); Todd K. Whitehurst, Sherman Oaks, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 80 days.

(21) Appl. No.: 09/761,934

(22) Filed: Jan. 17, 2001

Related U.S. Application Data
(60) Provisional application No. 60/184,561, filed on Feb. 24, 2000.

(51) Int. Cl.[7] .......................... A61B 19/00; A61M 5/178; A61M 31/00
(52) U.S. Cl. ............... 606/129; 604/164.01; 604/164.1; 604/59
(58) Field of Search ............................... 606/130, 129; 600/8, 7, 417, 429; 128/899; 604/57, 59, 60, 164.01, 164.1

(56) References Cited

U.S. PATENT DOCUMENTS

| | | | | |
|---|---|---|---|---|
| 3,352,306 A | * | 11/1967 | Hirsch .................... 604/164.01 |
| 3,884,220 A | * | 5/1975 | Hartnett ...................... 600/431 |
| 4,402,323 A | | 9/1983 | White ........................ 128/642 |
| 4,941,874 A | * | 7/1990 | Sandow et al. ............. 604/197 |
| 4,994,028 A | | 2/1991 | Leonard et al. ............... 604/60 |
| 5,193,539 A | * | 3/1993 | Schulman et al. ............. 607/61 |
| 5,248,301 A | * | 9/1993 | Koenig et al. ........... 604/164.01 |
| 5,300,079 A | | 4/1994 | Niezink et al. .............. 606/117 |
| 5,520,660 A | | 5/1996 | Loos et al. .................. 604/236 |
| 5,571,136 A | * | 11/1996 | Weaver ...................... 606/174 |
| 5,775,331 A | | 7/1998 | Raymond et al. ........... 128/741 |
| 5,882,331 A | * | 3/1999 | Sasaki ........................ 128/898 |
| 5,984,890 A | | 11/1999 | Gast et al. .................... 604/60 |
| 5,987,352 A | | 11/1999 | Klein et al. ................. 600/509 |
| 6,010,487 A | * | 1/2000 | DeMichele et al. .... 604/164.01 |
| 6,214,032 B1 | | 4/2001 | Loeb et al. .................... 607/1 |

\* cited by examiner

*Primary Examiner*—Michael J. Milano
*Assistant Examiner*—Gwen Phanijphand
(74) *Attorney, Agent, or Firm*—Laura Haburay Bishop; Bryant R. Gold

(57) ABSTRACT

A tool is provided for facilitating determining a proper location for an implantable device or medication, and for then delivering the implant to the precise location determined with the tool. To determine the target location, the tool may include a component for testing target locations, such as a stimulating probe for simulating a miniature implantable stimulator. In one embodiment, the tool is used to test a miniature implantable stimulator prior to depositing the implant precisely at the target location. The components of the tool are configured to maintain the implant at the target location while the tool is withdrawn. In one embodiment, a push rod assembly of the tool keeps the implant in position while it retracts the implant holder from around the implant. The ergonomic and light-weight tool leads to reduced surgical time, number and size of incisions, risk of infection, and likelihood of error.

32 Claims, 10 Drawing Sheets

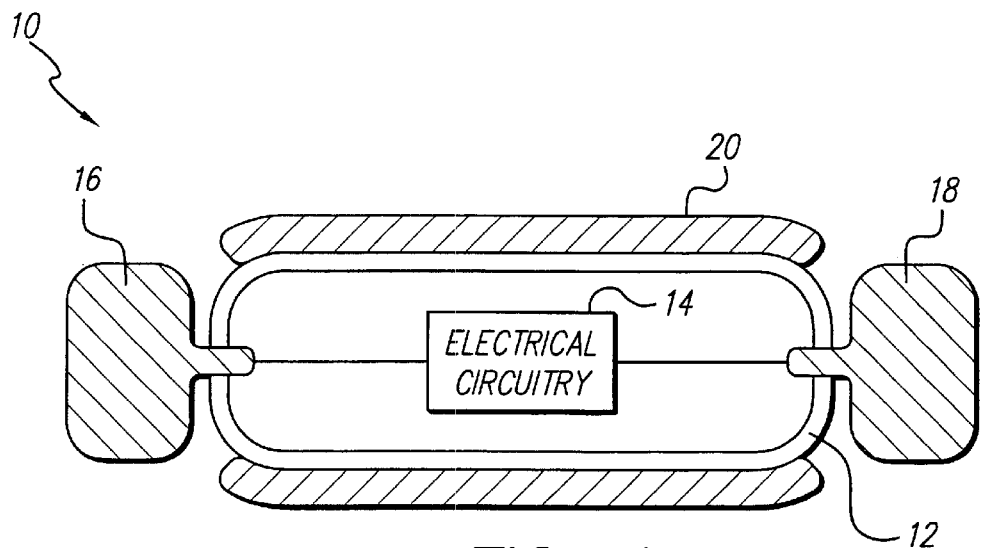

FIG. 1

LOCATE IMPLANT SITE (WHICH MAY INCLUDE DETERMINING AND/OR CONFIRMING SITE), COMPRISING USE OF ONE OR MORE DEVICES SUCH AS:
- STIMULATING PROBE
- ULTRASOUND PROBE
- TEMPERATURE PROBE
- ENDOSCOPE
- CHEMICAL SENSOR
- IMPLANT
- CANNULA
- HANDLE
- IMPLANT HOLDER
- PUSH ROD
- ETC.

DEPOSIT IMPLANT (WHICH MAY INCLUDE POSITIONING AND STABILIZING IMPLANT) AT SITE, COMPRISING USE OF ONE OR MORE DEVICES SUCH AS:
- IMPLANT HOLDER
- PUSH ROD
- CANNULA
- HANDLE
- ETC.

FIG. 14

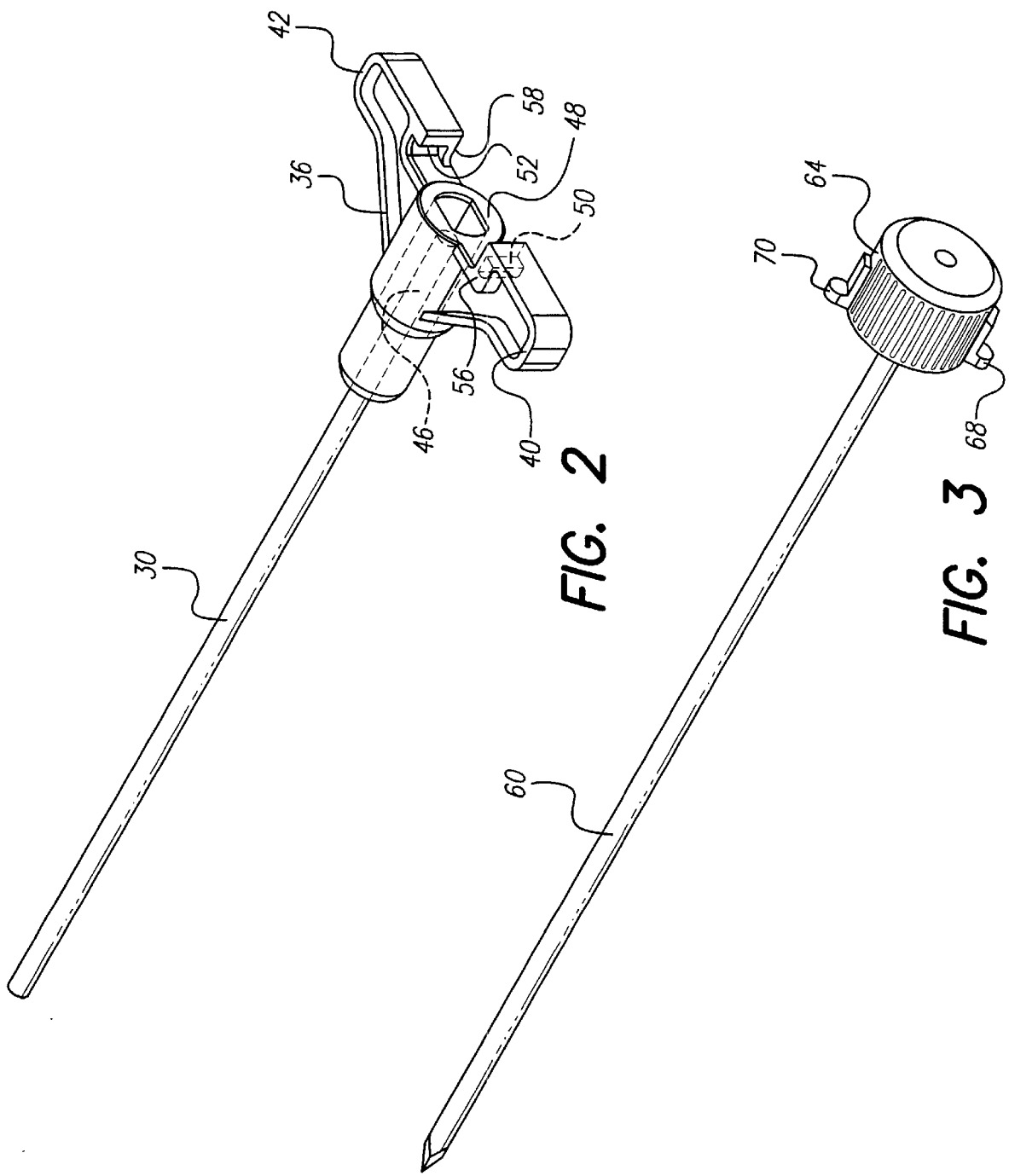

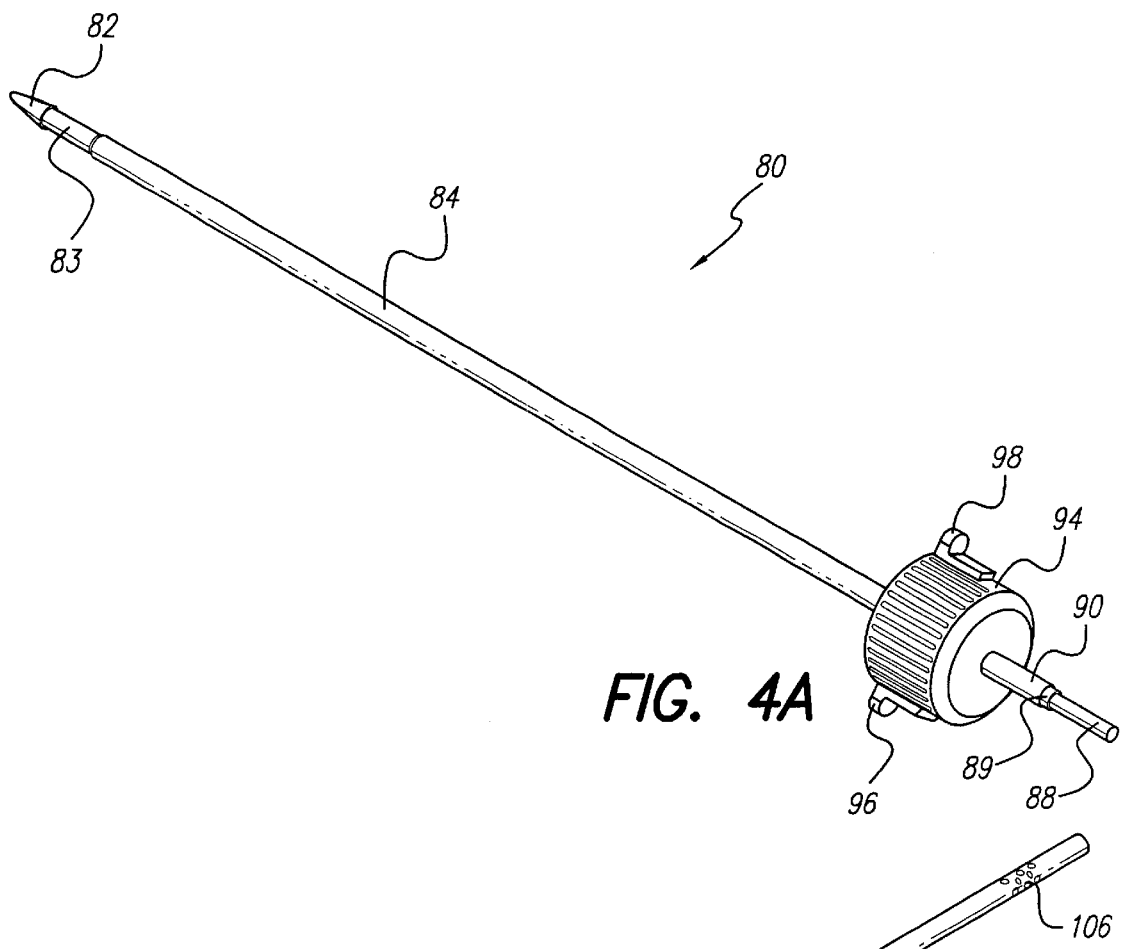
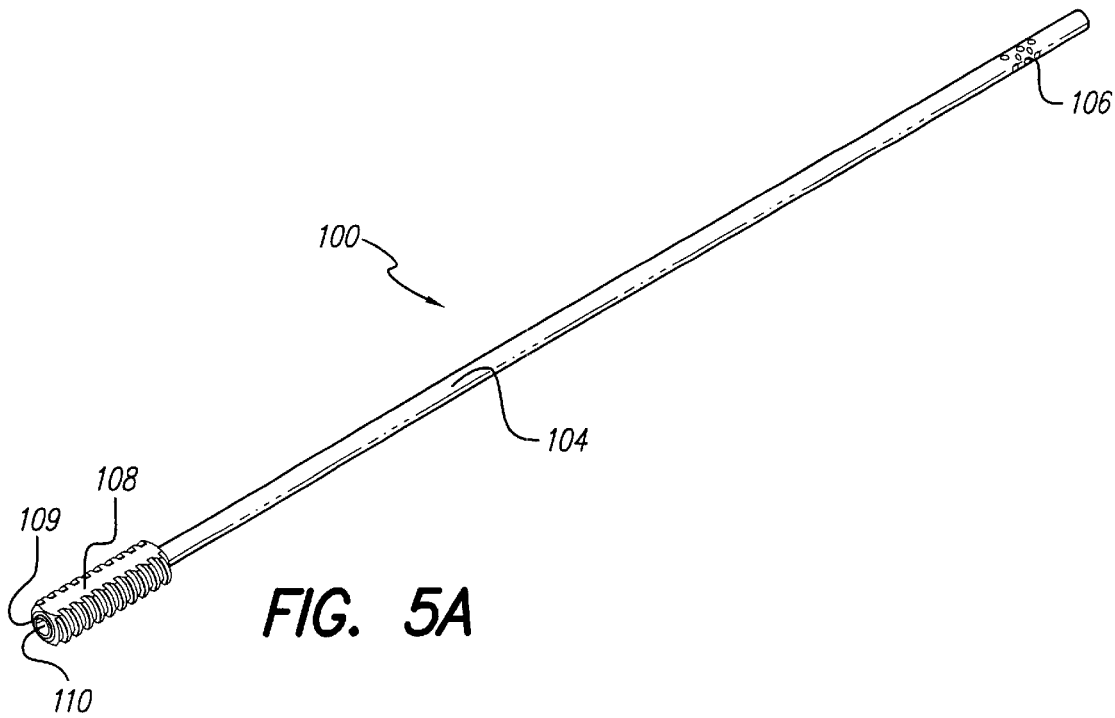

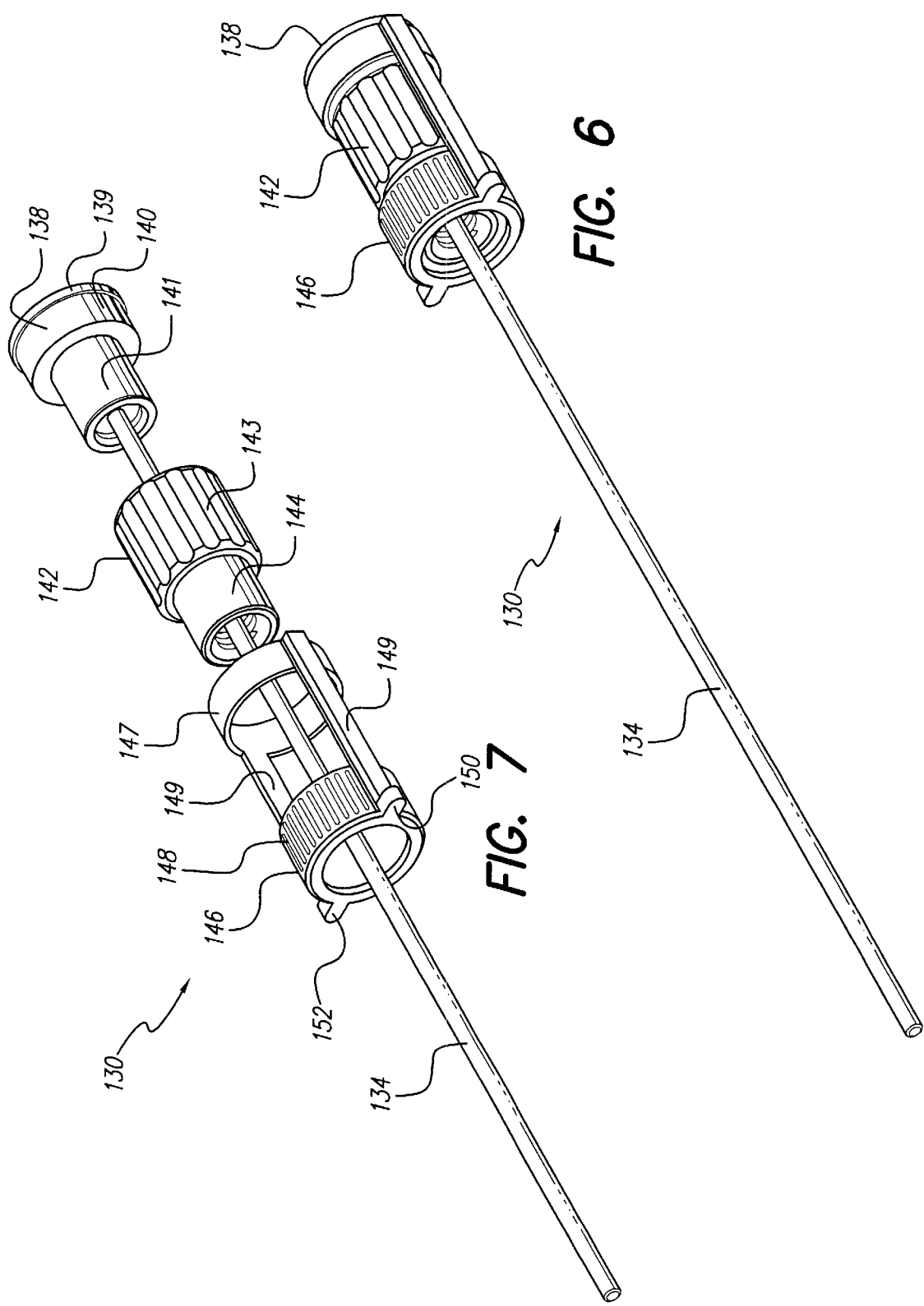

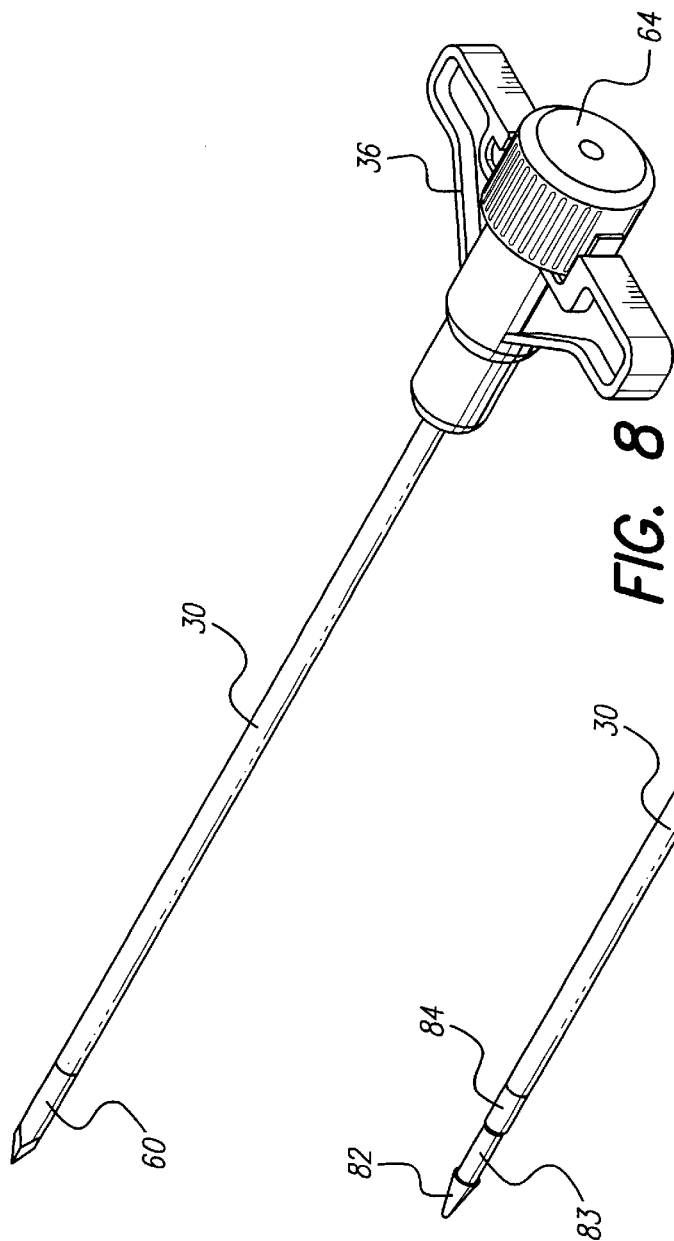

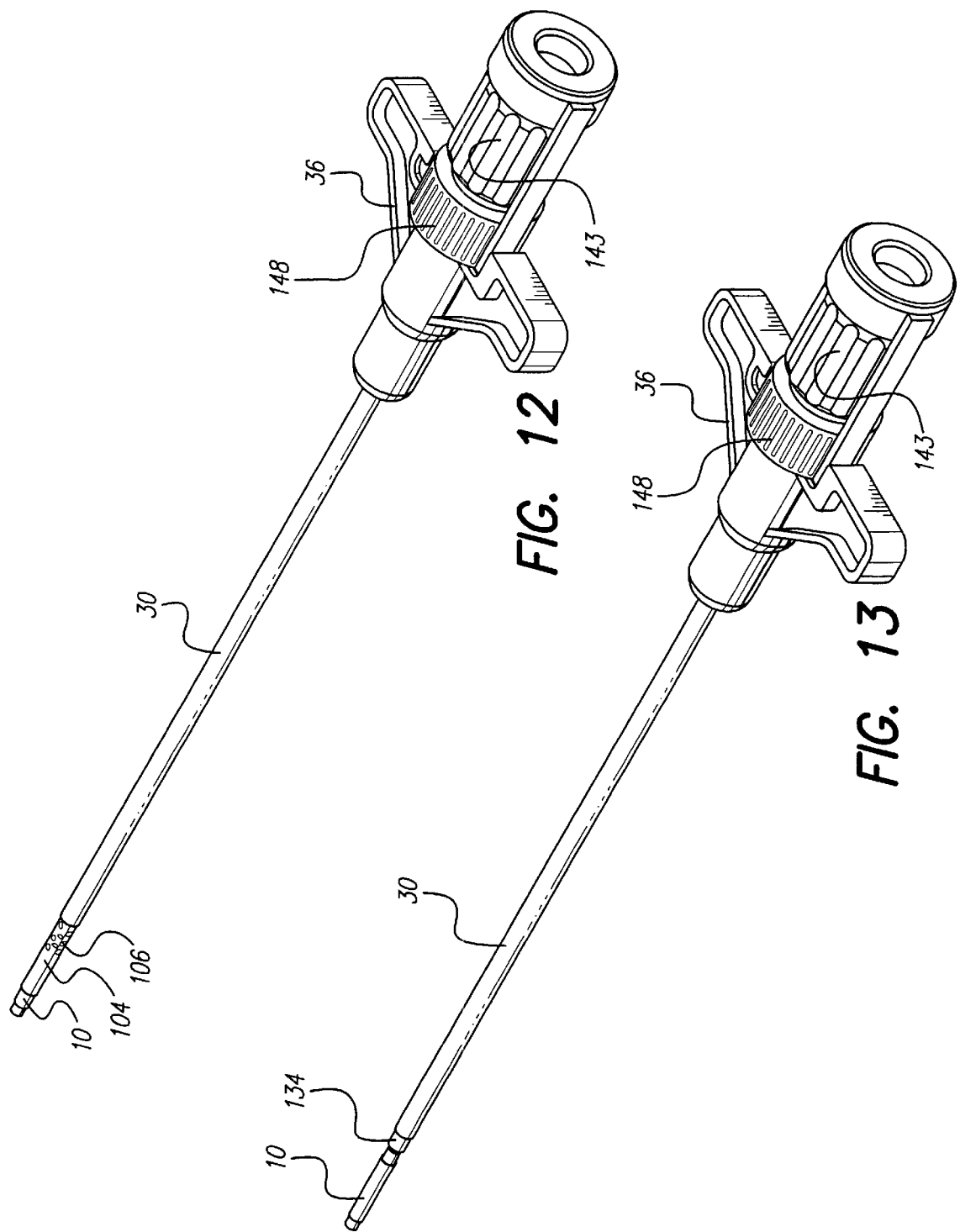

SURGICAL INSERTION TOOL

This application claims the benefit of U.S. Provisional Patent Application Serial No. 60/184,561, filed Feb. 24, 2000, which application is incorporated herein by reference.

FIELD OF THE INVENTION

The present invention generally relates to implantation of a medical device or medication in a living body, and more particularly relates to an insertion tool for implanting a medical device or medication in a living body.

BACKGROUND OF THE INVENTION

A variety of mechanisms exist for the implantation or injection of devices or medications within a living body. Items such as medicinal pellets or rods, contraceptive capsules, and sensors or identification transponders may be implanted at a target location within a human or other body. The associated procedures often employ multiple tools and/or specialized tools.

Known tools provide means for delivering an implant to a position determined by a surgeon or tool user as the correct location. Other tools are designed to deliver an implant to a position that is, in part, determined by the tool itself. For instance, mechanisms exist that control the angle of insertion or control the depth of insertion, and/or place the implant relative to the surface of the skin. With these tools, the site of tool insertion may still be determined by a surgeon, which may directly impact the final location of the implant. Still other procedures require a surgeon to determine the correct implant site using a first set of tools (which may or may not be invasive), and then to switch to the insertion tools required to deliver the implant. Unfortunately, the implant site determined by the first set of tools may not easily be located with the implant insertion tools.

Some implants, by their nature, do not require an exact location. For instance, a transponder that is injected into an animal may provide the intended tracking function, whether it is located under the skin of the ear, the neck, or the head. Other implants may require a higher degree of precision. This is the case for contraceptive rods that are implanted a specific distance from the surface of the skin, to facilitate later removal. Yet other implants require very precise placement in order to satisfy the intended function, such as devices using electrodes to stimulate specific nerves. If an electrode is not positioned close enough to stimulate the targeted nerve, additional surgery may be required.

While mechanisms exist for inserting or injecting implants in an approximate location (e.g., at a certain angle or depth), and other mechanisms exist for determining a target location for an implant, a need remains for a single, easy to use tool that is first used to determine or confirm the desired implant site and then reliably delivers the implant to that site. While procedures requiring very precise implant positioning will most benefit from such a tool, inserting implants requiring less precision will still find such a tool an improvement over the prior art mechanisms.

In addition, the implantation of microminiature, leadless stimulators called Bionic Neurons (also referred to as BIONs™ microstimulators) heretofore would have required the use of multiple surgical instruments and/or instruments not ideally suited for the insertion of such a device. Therefore, a need also exists for a tool that locates and/or confirms the proper implant site for a BION stimulator, and then inserts the BION stimulator at that location.

As is ideal for any surgical tool, a tool that provides the above benefits should also be easy and evident to use, so that surgical time and possibility of error are both decreased. Also, the tool should limit the number and size of incisions required, to reduce the likelihood of infection, loss of blood, post-surgical pain, etc. The tool is preferably compact, light-weight and ergonomic, and constructed of materials that may be sterilized by standard methods known in the art (e.g., autoclave sterilization).

BRIEF SUMMARY OF THE INVENTION

The present invention addresses the above and other needs by providing an insertion tool for a miniature implantable stimulator or other implantable device or medication.

The insertion tool of the present invention preferably applies to microminiature, leadless stimulators called BION™ stimulators or BION microstimulators or BION implants or BION devices. However, the invention may also be used to implant other devices or to insert a medicament. For use with a BION stimulator, the components of the tool preferably include a cannula which is used in conjunction with the remaining components to determine and/or confirm the proper implant location and then deliver the stimulator to that precise location.

In a primary embodiment, a trocar, scalpel, or other standard instrument is used to facilitate entry through the skin. A stimulating probe is inserted into the cannula of the tool and is used to bluntly dissect to the implant area. With the probe tip at a probable implant site, electrical impulses are delivered to the probe tip to test the area and determine and/or confirm the desired implant site. Once an acceptable site is found, the stimulating probe is removed from the cannula, and an implant holder containing a BION stimulator is inserted into the cannula. The implant is packaged and provided in the implant holder, which ensures proper electrical polarity, and helps protect and ease handling of the BION device.

A push rod assembly is positioned with the rod in the implant holder tube, so the distal end of the rod abuts the proximal end of the implant. The BION microstimulator is tested to ensure proper operation and position. Mating mechanisms on the implant holder and push rod assembly are utilized to pull the implant holder proximally from around the implant, while the push rod keeps the implant in position. With the implant holder thus retracted, the tool is removed, leaving the implant precisely in the proper location.

Other embodiments of the invention include various methods and tool configurations for determining and/or confirming a proper implant site. In addition, alternative mechanisms and methods for removal of the implant holder from around the implant are described, as are alternatives for streamlined use with the BION stimulator or with implants other than a microstimulator.

BRIEF DESCRIPTION OF THE SEVERAL VIEWS OF THE DRAWINGS

The above and other aspects, features, and advantages of the present invention will be more apparent from the following more particular description thereof, presented in conjunction with the following drawings wherein:

FIG. 1 diagrammatically illustrates, as an example of a device or medication which may be implanted with the tool of the present invention, one embodiment of an implantable BION microstimulator;

FIG. 2 is a perspective view of a cannula and handle of an embodiment of the tool of the present invention;

FIG. 3 is a perspective view of a trocar and trocar cap that make up an optional component of the tool of the present invention;

FIG. 4A is a perspective view of one configuration of a stimulating probe of an embodiment of the present invention;

FIG. 5A is a perspective view of an implant holder and implant holder head of an embodiment of the present invention;

FIG. 6 is a perspective view of a plastic push rod assembly of the tool of the present invention;

FIG. 7 is an exploded perspective view of the push rod assembly of FIG. 6;

FIG. 8 is a perspective view of the trocar of FIG. 3 in place within the cannula of FIG. 2, with the trocar cap secured to the handle of the tool of the present invention;

FIG. 9A is a perspective view of the stimulating probe of FIG. 4A in place within the cannula of FIG. 2, with the stimulating probe cap secured to the handle of the tool of the present invention;

FIG. 12 is a perspective view of the push rod assembly of FIG. 6 and implant holder (with implant at distal end) of FIG. 10 secured to the handle, prior to activation of the push rod; and FIG. 13 is a perspective view of the push rod assembly and implant holder of FIG. 12 after activation of the push rod, and shows the deposited implant of FIG. 1 detached from the distal end of the implant holder of FIG. 5A.

FIG. 14 is a block diagram that illustrates general use of a typical surgical tool of the invention, and illustrates some of the various uses of possible components of a typical surgical tool of the invention.

Corresponding reference characters indicate corresponding components throughout the several views of the drawings.

DETAILED DESCRIPTION OF THE INVENTION

Figure 4B:
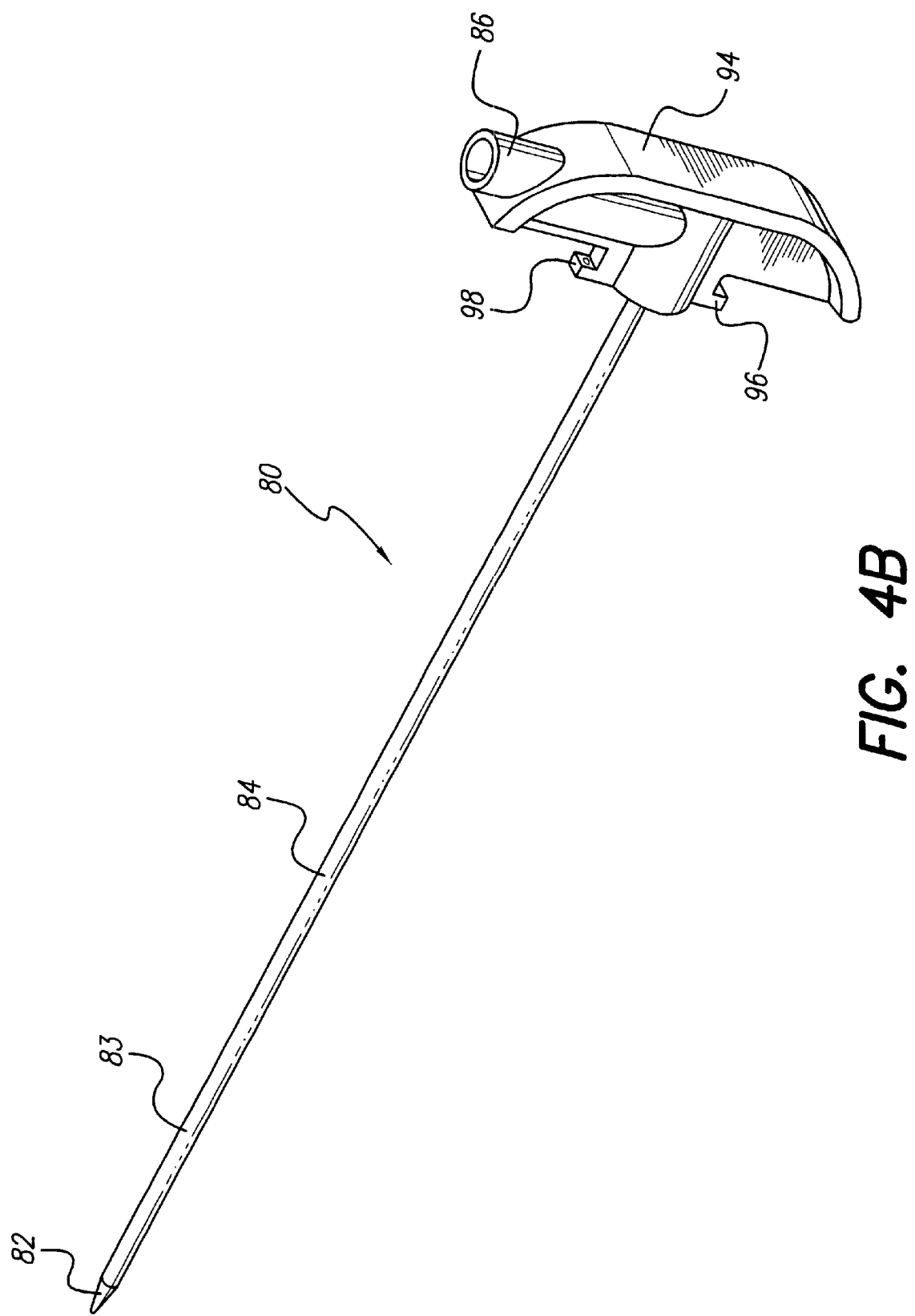
FIG. 4B is a perspective view of another configuration of a stimulating probe of an embodiment of the present invention.
Figure 5C:
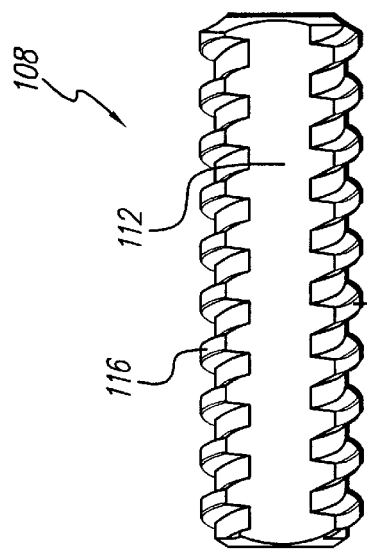
FIG. 5C is top view of the implant holder head of FIGS. 5A and 5B.
Figure 5E:
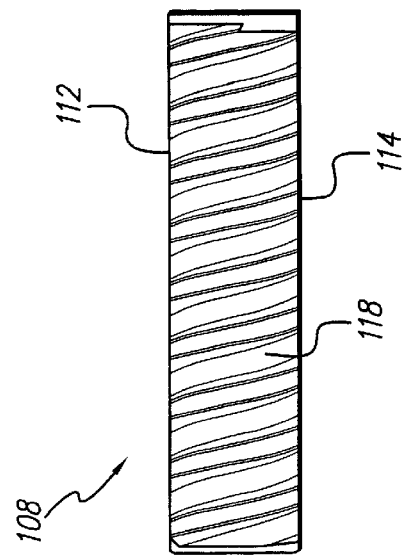
FIG. 5E is a side view of the implant holder head of FIGS. 5A, 5B, 5C, and 5D.
Figure 5B:
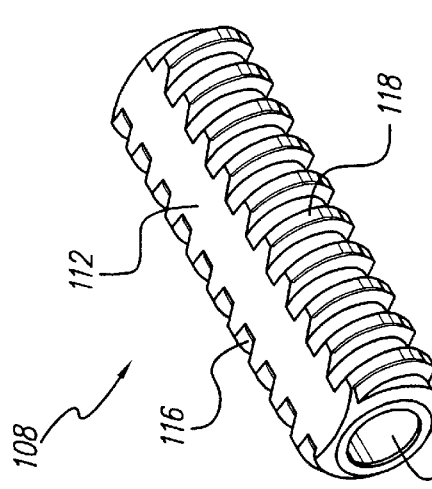
FIG. 5B is a perspective view of the implant holder head of FIG. 5A.
Figure 5D:
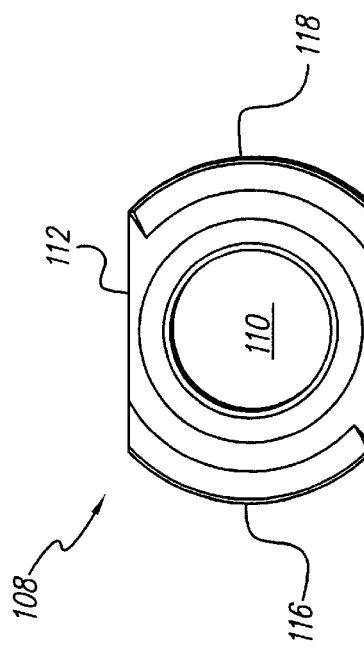
FIG. 5D is an end view of the implant holder head of FIGS. 5A, 5B, and 5C.

The following description is of the best mode presently contemplated for carrying out the invention. This description is not to be taken in a limiting sense, but is made merely for the purpose of describing the general principles of the invention. The scope of the invention should be determined with reference to the claims.

For illustration purposes, the following description of the present invention is shown in conjunction with a microminiature, implantable, leadless stimulator 10, such as a BION™ microstimulator, illustrated, e.g., in FIG. 1. The device 10 includes a narrow, elongated capsule 12 containing electronic circuitry 14 connected to electrodes 16 and 18, which pass through the walls of the capsule at either end, together forming a microstimulator of the type disclosed and fully described in U.S. Pat. Nos. 5,193,539 and 5,193,540, both of which are incorporated herein, in their entirety, by reference. As detailed in the referenced patents, and mentioned later herein, electrodes 16 and 18 comprise a stimulating electrode (to be placed close to the nerve) and an indifferent electrode (for completing the circuit) of a bipolar stimulator. Other configurations of device 10 are possible, as is evident from the above-referenced patents, such as a monopolar stimulator of the same general shape. The tool of the present invention is useful for inserting implants with shapes similar to device 10, and may be adapted for inserting implants of other shapes as well. Therefore, as will be evident to those of skill in the art, the claimed invention is useful for inserting a variety of implantable devices and medicaments.

The preferred surgical insertion tool of the present invention comprises a number of components, each of which is described below in connection with the Figures. FIG. 2 shows a first component of the tool of the present invention. Cannula 30 extends in a distal direction from handle 36. Cannula 30 is made of a medical grade material, with walls as thin as possible while still maintaining enough strength for its intended purposes (e.g., from 0.18 to 0.25 mm wall thickness), as described herein. In addition, it is preferred that this component of the tool, along with others, be durable enough to be reusable. Thus, cannula 30 may be made of plastic, but is preferably made of metal, such as stainless steel needle stock, and more preferably is made of titanium. The diameter of cannula 30 is preferably in the range of 1 mm to 10 mm, is more preferably between 1 mm and 5 mm, and most preferably about 3 mm to 4.5 mm.

Handle 36 is preferably made of injection molded plastic such as polyurethane, ABS, or polypropylene. The handle and cannula are affixed with any appropriate method. For instance, any suitable adhesive may be used (such as Prism 401, available from Loctite Corporation of Rocky Hill, Conn.). More preferably, cannula 30 is placed in a mold as a mold insert, and handle 36 is injection molded onto the proximal end of cannula 30. Handle arms 40 and 42, extending from opposite sides of the handle, are configured to be easy to grip, durable, and lightweight.

Extending axially within handle 36 outward toward the proximal end of the handle is channel 46. The opening to channel 46 is inset slightly from the proximal end of handle arms 40 and 42, along a plane defined by surface 48. On the portions of the handle arms extending proximally from surface 48 are notches 50 and 52. Notch 50 is open toward the bottom side of handle 46, with a stop or wall 56 on the upper side of the handle. Notch 52 is open toward the top side of handle 46, with a stop or wall 58 on the bottom side of the handle. As described in more detail below, notches 50 and 52 with stops 56 and 58 provide a mechanism for retaining components inserted through channel 46 into cannula 30.

Turning now to FIG. 3, an optional tool component, trocar 60 is shown with trocar cap 64 affixed at the proximal end of the trocar. On either side of trocar cap 64 are trocar cap tabs 68 and 70. Trocar 60 preferably has a sharp tip and is preferably made in a conventional manner and from conventional materials, such as 304 or 316 stainless steel. Trocar cap 64 is preferably made of injection molded plastic such as polyurethane, ABS, or polypropylene. Trocar cap 64 is affixed to trocar 60 via any appropriate methods. For instance, trocar cap 64 may be adhered to trocar 60 with any suitable adhesive (such as Loctite Prism 401). More preferably, trocar 60 is placed in a mold as a mold insert, and trocar cap 64 is injection molded onto the proximal end of trocar 60. Trocar 60 may extend entirely through trocar cap 64, or trocar cap 64 may completely surround the proximal end of trocar 60.

During the implant procedure, the surgeon decides whether to use the trocar, as described in more detail presently. If the trocar is used, trocar 60 is inserted through channel 46 of handle 36, and into cannula 30 until the distal end of trocar cap 64 contacts surface 48. The distal end of trocar 60 extends beyond the distal end of cannula 30. Once inserted, trocar cap 64 is turned clockwise until tabs 68 and 70 slide into notches 50 and 52, respectively. In this manner, trocar 60 is secured within cannula 30 until such times as trocar cap 64 is turned counter-clockwise, allowing trocar 60 to be removed from the cannula. Use of trocar 60 and all other components of the tool of the present invention are described presently, after an introduction to and description of the remaining components of the first embodiment of the invention, as continued below.

FIGS. 4A and 4B illustrate embodiments of a stimulating probe 80, which is a next component of the tool of the present invention. The stimulating probe 80 of FIG. 4A, which may be used to simulate bipolar stimulation, comprises coaxially arranged blunt tip 82, tube 84, tip insulator 83, tip extension 88, tube extension 90, insulator extension 89, and stimulating probe cap 94. The stimulating probe 80 of FIG. 4B, which may be used to simulate monopolar stimulation, comprises coaxially arranged blunt tip 82, tip insulator 83, tube 84, connection jack 86, and stimulating probe cap 94. Probe cap tabs 96 and 98 protrude from either side of probe cap 94 in FIGS. 4A and 4B.

In the preferred embodiment depicted in FIG. 4A, blunt tip 82 is formed at the distal end of tip extension 88, which together extend the full length of probe 80. Tip extension 88 and blunt tip 82 are preferably machined as one piece from a medical grade conducting material, such as 304 or 316 stainless steel. Alternatively, blunt tip 82 may be machined separately and affixed to a rod of stainless steel, for example, by welding or soldering them together. The radius of blunt tip 82 is preferably within the range of 0.25 mm to 1.75 mm, and is more preferably about 0.635 mm.

Still referring to FIG. 4A, tip insulator 83 is preferably the distal end of insulator extension 89. Insulator extension 89 and tip insulator 83 are preferably made of heat shrinkable insulating tubing formed in place via conventional methods around tip extension 88. Alternatively, the insulation may be formed by dipping tip extension 88 into a molten plastic, such as polyurethane. Blunt tip 82 preferably protrudes slightly from the distal end of tip insulator 83, and the proximal end of tip extension 88 preferably protrudes from the proximal end of insulator extension 89. The insulating tubing is preferably made of a fluoropolymer material such as polytetrafluoroethylene (PTFE), and most preferably is made of a Teflon® material.

As seen in FIG. 4A, around the outside of the insulating tubing and extending nearly to the ends of the insulating tubing is tube 84. Tube extension 90 is preferably the proximal end of tube 84. Tube 84 and tube extension 90 are preferably made of medical grade metal, such as stainless steel needle stock. The distal end of tip insulator 83 preferably protrudes from the distal end of tube 84, and the proximal end of insulator extension 89 preferably protrudes from the proximal end of tube extension 90.

Probe cap 94 of FIG. 4A is preferably made of injection molded plastic such as polyurethane, ABS, or polypropylene, and is affixed around tube 84 with any appropriate method. For instance, any suitable adhesive may be used (such as Loctite Prism 401). More preferably, once tip 82 and its extension 88, tip insulator 83 and its extension 89, and tube 84 and its extension 90 are formed, they are placed in a mold as a mold insert, and probe cap 94 is injection molded onto tube 84, with the proximal end of tube 84 extending beyond the proximal end of probe cap 94. Alternatively, tube 84 and its extension 90 (which are assembled with tip 82 and its extension 88 and tip insulator 83 and its extension 89) are interference fit into a hole in probe cap 94. This assembly allows electrical stimulation access to blunt tip 82 via tip extension 88 and to tube 84 via tube extension 90. This is described in detail presently.

In the preferred embodiment depicted in FIG. 4B, blunt tip 82 is positioned at the distal end of tube 84. Tube 84 and blunt tip 82 may be machined as one piece from a medical grade conducting material, such as 304 or 316 stainless steel. Alternatively, blunt tip 82 may be machined separately and fixed to a rod of stainless steel, for example, with conductive adhesive, or they may be welded or soldered together. In this case, tube 84 is preferably made of 11 RW gauge hypodermic tube, or the like. As with FIG. 4A, the radius of blunt tip 82 is preferably within the range of 0.25 mm to 1.75 mm, and is more preferably about 0.635 mm.

Still referring to FIG. 4B, tip insulator 83 is preferably made of heat shrinkable insulating tubing formed in place via conventional methods around tube 84. Alternatively, the insulation may be formed by dipping tube 84 into a molten plastic, such as polyurethane. Blunt tip 82 preferably protrudes slightly from the distal end of tip insulator 83. As with FIG. 4A, the insulating tubing is preferably made of a fluoropolymer material such as polytetrafluoroethylene (PTFE), and most preferably is made of a Teflon® material.

Probe cap 94 of FIG. 4B is preferably made of injection molded plastic such as polyurethane, ABS, or polypropylene, and is affixed around the proximal end of tube 84 with any appropriate method. For instance, any suitable adhesive may be used (such as Loctite Prism 401). More preferably, tube 84 (before or after assembly with tip 82 and tip insulator 83) is placed in a mold as a mold insert, and probe cap 94 is injection molded onto the proximal end of tube 84. Alternatively, tube 84 (before or after assembly with tip 82 and tip insulator 83) is interference fit into a blind hole in probe cap 94.

Probe cap 94 of FIG. 4B includes a connection jack 86, which allows electrical stimulation access to blunt tip 82 via tube 84. Connection jack 86 may be formed in probe cap 94 by any number of different means. For instance, thin wall tubing, such as 7 gauge stainless steel tubing may be welded or soldered to tube 84 prior to forming probe cap 94. Insertion molding, as described previously, may then be used to form probe cap 94 over the proximal end of tube 84 and around connection jack 86, leaving the end of connection jack 86 exposed as shown in FIG. 4B. In another alternative, connection jack 86 comprises a screw, such as a ¼ 28×¾ self tapping hex socket head cap screw made of stainless steel or the like, with a hole of about 4 mm (0.16 inch) diameter drilled through its length. Probe cap 94 may be formed with a hole where the self tapping screw may later be screwed into place so that the distal end of the screw contacts tube 84 and the proximal end of the screw is exposed. Other connection jack configurations are possible as one of skill in the art will recognize upon reading the above alternatives. Electrical stimulation through connection jack 86 is described in more detail presently.

In a similar manner as with trocar 60, during operation, probe 80 of either FIG. 4A or 4B is inserted through channel 46 of handle 36, and into cannula 30 until the distal end of probe cap 94 contacts surface 48. The distal end of tube 84, the distal end of tip insulator 83, and blunt tip 82 extend beyond the distal end of cannula 30. Once inserted, probe cap 94 is turned clockwise until tabs 96 and 98 slide into notches 50 and 52, respectively. In this manner, probe 80 is secured within cannula 30 until such times as probe cap 94 is turned counter-clockwise, allowing probe 80 to be removed from the cannula.

Another component of the tool, implant holder 100, is shown in FIG. 5. Holder 100 includes a holder tube 104 that is preferably made of material that is slightly elastic, but with sufficient mechanical strength for the uses described below. In particular, for the primary embodiment, the material from which holder tube 104 is made preferably has little or no interference with external signals (e.g., radio frequency (RF) signals) that may be used to test the implant while the implant is still positioned in the implant holder. Thus, holder tube 104 is preferably made of medical grade polymer, such as silicon rubber, or more preferably is made of a thin-walled fluoropolymer material such as PTFE, and most preferably is made of a Teflon® material. Holder tube 104 is preferably made via a conventional method, such as injection molding, or more preferably by extrusion.

Near the distal end of hollow holder tube 104 is preferably a series of holes 106. As will become apparent presently, holes 106 are useful when implanting microstimulator 10, but may not be necessary or desired when implanting other devices or medications. Holes 106 may be formed by conventional methods, such as during injection molding of holder tube 104, or more preferably are formed by machining (e.g., the holes may be punched) during the extrusion process.

Secured to, or preferably around, the proximal end of holder tube 104 is holder head 108. Holder head 108 is preferably made of injection molded plastic such as polyurethane, ABS, or polypropylene. Holder head 108 and holder tube 104 are affixed with any appropriate method. For instance, any suitable adhesive may be used (such as Loctite Prism 401). If tube 104 is made of a Teflon® material, for example, it is helpful to first etch or otherwise prime the tube before applying an adhesive. Depending on the material chosen for tube 104, the tube may alternatively be placed in a mold as a mold insert, and head 108 may be injection molded onto the proximal end of tube 104. Alternatively, holder head 108 is held in place on holder tube 104 using an interference fit. Preferably, a tube insert 109 that is approximately the length of holder head 108 is placed in the proximal end of holder tube 104. Insert 109 preferably has an outer diameter slightly greater than the inner diameter of holder tube 104. Where insert 109 is positioned, holder tube 104 expands enough to securely retain holder head 108 on holder tube 104. Insert 109 is thus preferably made of a stiff metallic or plastic material, and more preferably is made of stainless steel or the like.

The proximal ends of holder tube 104, holder head 108, and insert 109 are preferably, but not necessarily coincident. Passage 110 through holder head 108 and insert 109 allows access to the inside of hollow implant holder tube 104. The inner diameter of the distal end of holder tube 104 is preferably slightly smaller than the outer diameter of the implant, allowing for an interference fit that holds the implant securely in the tube until intentional release of the implant.

During operation, implant holder 100, while holding an implantable medication or device, such as stimulator 10, is inserted through channel 46 of handle 36 and into cannula 30. Alternatively, the implant may be placed into the distal end of implant holder 100 after the holder is inserted into cannula 30. When fully inserted, the distal end of holder head 108 preferably abuts the distal end of channel 46 and the proximal end of head 108 preferably extends beyond surface 48 and the proximal end of channel 46. The proximal end of head 108 preferably extends beyond surface 48 enough for proper interaction with other components of the tool, as described presently. The distal end of holder tube 104 (and an implant held by the tube) preferably extend beyond the distal end of cannula 30.

Unintended rotation of implant holder 100 within cannula 30 is preferably prevented by virtue of the shape of implant head 108 mating to the shape of channel 46. For example, head 108 preferably comprises a screw with a double lead thread, with the threads along two opposite sides removed, resulting in opposing, parallel, flat surfaces 112 and 114 along the axis of head 108, as best seen in FIGS. 5B, 5C, 5D and 5E. Flat surfaces 112 and 114 and opposing threaded portions 116 and 118 mate with the similarly shaped channel 46 (FIG. 2). Advantageously, the double lead thread reduces the number of turns required for activation, thus a triple or greater lead thread may also be used. Those of skill in the art will recognize that other configurations of implant holder and handle may be used, including less preferable configurations that allow the implant holder to rotate while engaged within the cannula.

Turning now to FIGS. 6 and 7, push rod assembly 130 of the tool of the present invention is shown. The configuration of items shown in FIG. 7 is for clarification only; in operation, the pieces of push rod assembly 130 do not separate in this manner. Push rod assembly 130 comprises coaxially arranged rod 134, rod cap 138, driving wheel 142, and housing 146.

Rod 134 is preferably made of a rigid or semirigid medical grade material that resists deformation. Thus, rod 134 may be made of metal, such as stainless steel, or it may be made silicon, but is more preferably made of plastic such as nylon or polyethylene, and is most preferably made of polyether ether ketone (PEEK). Rod 134 is preferably formed via a conventional method, such as extrusion. Rod 134 may be hollow or solid, but must be stiff enough for its intended purpose, described below.

Secured to, or preferably around, the proximal end of rod 134 is rod cap 138. Rod cap 138 is preferably made of injection molded plastic such as polyurethane, ABS, or polypropylene. Rod cap 138 and rod 134 are affixed with any appropriate methods. For instance, any suitable adhesive may be used (such as Loctite Prism 401). More preferably, the rod 134 is placed in a mold as a mold insert, and rod cap 138 is injection molded onto the proximal end of rod 134. Alternatively, rod 134 is interference fit into a blind hole in rod cap 138. The proximal end of rod 134 and the proximal end of rod cap 138 are preferably, but not necessarily coincident. In other words, rod 134 may extend entirely through rod cap 138, or rod cap 138 may completely surround the proximal end of rod 134.

Rod cap 138 preferably has three sections along its axis. At the proximal end of rod cap 138 is cap end section 139, which preferably has a slightly larger diameter than cap center section 140, which is attached to the distal side of cap end section 139. Similarly, cap center section 140 preferably has a larger diameter than cap insert section 141, which is attached to the distal side of cap center section 140. Preferably, the three sections of rod cap 138 are formed as one piece (via, e.g., injection molding).

Driving wheel 142 preferably has two sections along its axis. At the proximal end of driving wheel 142 is wheel knob section 143. Wheel knob section 143 of driving wheel 142 is preferably rotatable and slidable over cap insert section 141 of rod cap 138, and preferably has knurling, ribs, or other surface features or texture that helps prevent slipping during actuation. When driving wheel 142 is slid or rotated over cap insert section 141 toward the proximal end of push rod assembly 130, the proximal end of wheel knob section 143 abuts the distal end of cap center section 140. At the distal end of driving wheel 142 is wheel insert section 144, which preferably has a smaller diameter than wheel knob section 143. At the distal end of wheel insert section 144 is an opening with female threads used to engage the double lead thread on holder head 108, as described later. The two sections of driving wheel 142 are preferably formed as one piece via a conventional method, such as injection molding, out of plastic such as polyurethane, ABS, or polypropylene.

At the proximal end of housing 146 is housing end section 147. At the distal end of housing 146 is housing grip section 148. Housing grip section 148 preferably has knurling, ribs, or other surface features or texture that helps the operator hold the tool securely. Between housing end section 147 and housing grip section 148 are connector members 149. Connector members 149 are preferably narrow, to allow easy access to and manipulation of wheel knob section 143. Protruding from the distal end of connector members 149 are housing tabs 150 and 152. All sections of housing 146 are preferably formed as one piece via a conventional method, such as injection molding, out of plastic such as polyurethane, ABS, or polypropylene.

During assembly, rod cap 138 is first affixed (via a method previously described) to rod 134. Next, driving wheel 142 is placed over the distal end of rod 134 and is slid over cap insert section 141 until the proximal end of wheel knob section 143 abuts the distal end of cap center section 140. Then, housing 146 is placed over the distal end of rod 134 and slid over driving wheel 142 until the proximal end of housing end section 147 abuts the distal side of cap end section 139. Thus, once assembled, housing end section 147 surrounds cap center section 140. Housing end section 147 is preferably further secured to cap center section 140 via adhesive (e.g. Loctite Prism 401) or other suitable method. Housing grip section 148 fits over wheel insert section 144 so that cap insert section 141 and housing components 148 and 149 hold driving wheel 142 in place. Driving wheel 142 is preferably able to rotate and slide over cap insert section 141 toward the distal end of push rod assembly 130, so the female threads inside wheel insert section 144 can readily engage the double lead thread on holder head 108. Connector members 149 establish a space between housing end section 147 and housing grip section 148 that is preferably slightly greater than the length of wheel knob section 143. In addition, the distance between the inner surfaces of connector members 149 is slightly larger than the outer diameter of wheel knob section 143, which preferably has an outer diameter that is comfortable for rotation with fingers. This configuration allows wheel knob section 143 to slide axially and to rotate over cap insert section 141.

During operation, rod 134 of push rod assembly 130 is inserted into holder tube 104 of implant holder 100 (implant holder 100 was previously positioned in cannula 30 with holder head 108 protruding from channel 46 of handle 36). When push rod assembly 130 is fully inserted, the distal end of housing grip section 148 contacts surface 48, holder head 108 protrudes into the opening at the distal end of grip section 148, and the distal end of rod 134 preferably contacts, or nearly contacts, the proximal end of implant 10 (which was previously positioned in the distal end of holder tube 104). Housing 146 is then turned clockwise until tabs 150 and 152 slide into notches 50 and 52, respectively. In this manner, rod 134 is secured within holder tube 104 until such times as housing 146 is turned counter-clockwise, allowing push rod assembly 130 to be removed.

Use of the tool of the preferred embodiment with a miniature, implantable, leadless stimulator 10 (i.e., a BION stimulator) is now described. As mentioned earlier, this description of the present invention is shown in conjunction with a BION microstimulator for illustration purposes; the tool of the present invention is useful for a variety of devices and medications.

After topical anesthetic is applied, known methods are used to identify the optimal surgical approach and to confirm the target nerve is intact. For instance, a 24-gauge needle electrode attached to a commercial neurostimulator may be used. For entry through the skin, any acceptable method may be used. For instance, a scalpel with a #7 scalpel blade, or any other suitable blade, may be used.

Alternatively, optional tool component trocar 60 may be used to facilitate entry through the skin. In this case, trocar 60 is inserted into cannula 30 and trocar cap 64 is secured to handle 36 as previously described. Then, with the trocar in place within the cannula (FIG. 8), the skin is penetrated. Trocar 60 may be used to dissect the approach to the implant location, or preferably blunt tip 82 of stimulating probe 80 is used for this purpose. Once trocar 60 (and thus cannula 30) is in the desired position, trocar cap 64 is rotated counter-clockwise, and trocar 60 is pulled in a proximal direction while handle 36 is held steady. In this manner, trocar 60 is removed from cannula 30 while maintaining the position of cannula 30.

Stimulating probe 80 is inserted into cannula 30 and probe cap 94 is secured to handle 36 (FIGS. 9A and 9B) as described earlier. For the preferred embodiment, the stimulating probe comprises a blunt tip as indicated earlier, but a sharper or blunter tip may be useful in some situations. Stimulating probe 80 is maneuvered until tip 82 is believed to be near where the implant may ultimately be located. A commercial neurostimulator is then attached to the stimulating probe 80 of FIG. 9A by securing stimulating wires (via an alligator clip or the like, not shown) to tip extension 88, and return path wires (via an alligator clip or the like, not shown) to tube extension 90. This provides bipolar stimulation, which may be necessary or desired in certain situations. If monopolar stimulation is necessary or desired, a commercial neurostimulator may be attached to the stimulating probe 80 of FIG. 9B by inserting a plug or the like (not shown) into connection jack 86. A wet pad or the like attached to the skin provides the return.

Figure 9B:
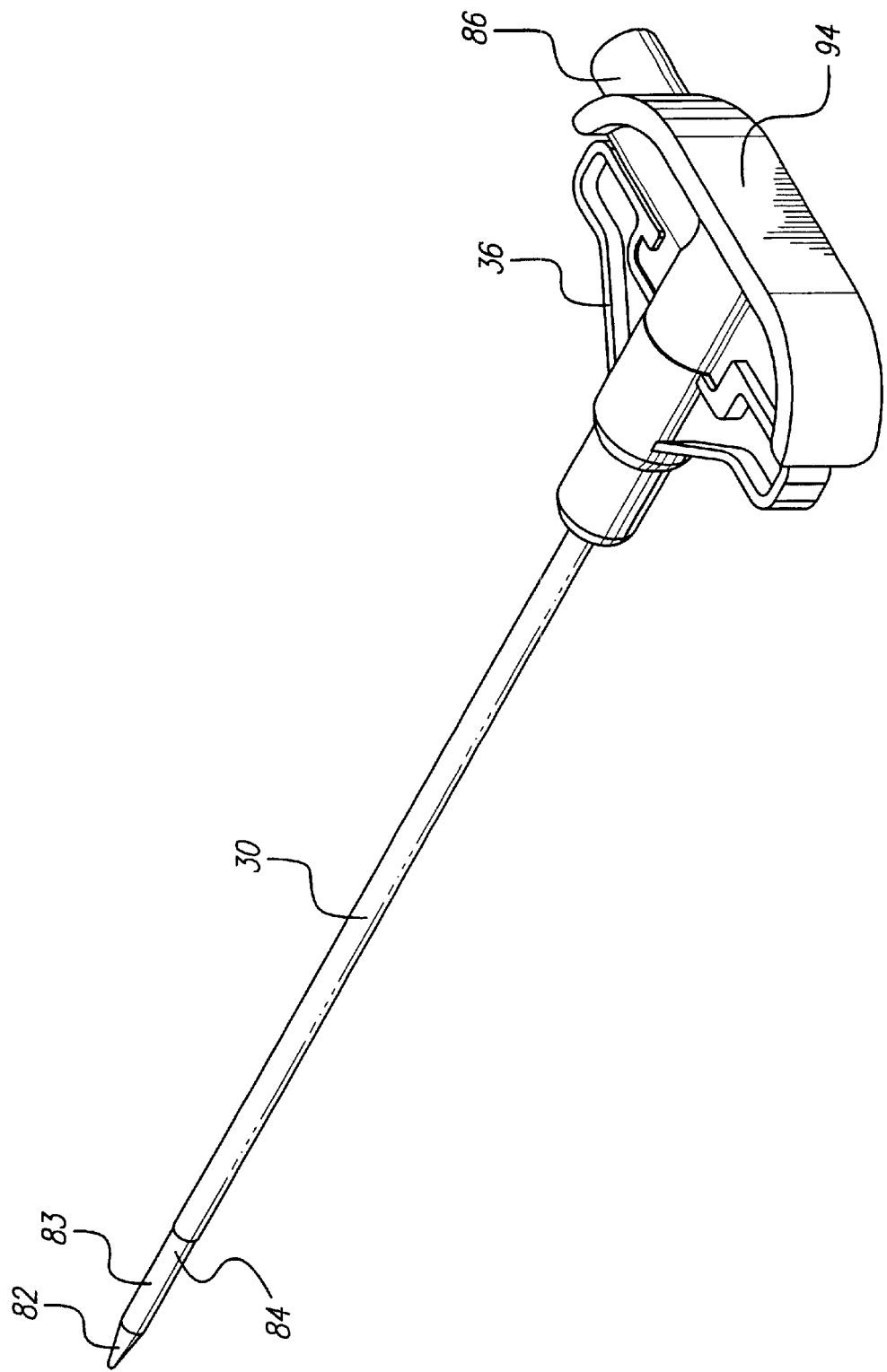
FIG. 9B is a perspective view of the stimulating probe of FIG. 4B in place within the cannula of FIG. 2, with the stimulating probe cap secured to the handle of the tool of the present invention.

With the distal end of probe 80 near the target location, the commercial neurostimulator is activated. This sends stimulating pulses from tip extension 88 (FIG. 9A) or from connection jack 86 and tube 84 (FIG. 9B) down to blunt tip 82, which acts as the stimulating electrode. For simulating bipolar stimulation, the distal end of tube 84 of FIG. 9A acts as the indifferent electrode, and sends the electrical impulses it receives up to tube extension 90. For simulating monopolar stimulation, the arrangement shown in FIG. 9B is used with a wet pad affixed to the skin, which provides the return, as described earlier.

Preferably, blunt tip 82 is located the same distance from the distal end of cannula 30 as the stimulating electrode of the BION stimulator when held in place by the implant holder 100. In addition, for simulating bipolar stimulation, the distance between blunt tip 82 and the distal end of tube 84 (FIG. 9A) is preferably equivalent to the distance between electrodes 16 and 18 of the microstimulator. If so, this procedure provides a good representation of the stimulation of a BION microstimulator delivering bipolar stimulation.

The amplitude is increased until the patient senses the stimulation (i.e., until the patient's sensory threshold is reached). The probe tip is then maneuvered until tip 82 is positioned at the location with the lowest sensory threshold (i.e., where the greatest sensation is felt). Probe cap 94 is rotated counter-clockwise and probe 80 is pulled in a proximal direction while handle 36 is held steady. In this manner, probe 80 is removed from cannula 30 while maintaining the position of cannula 30.

Figure 10:
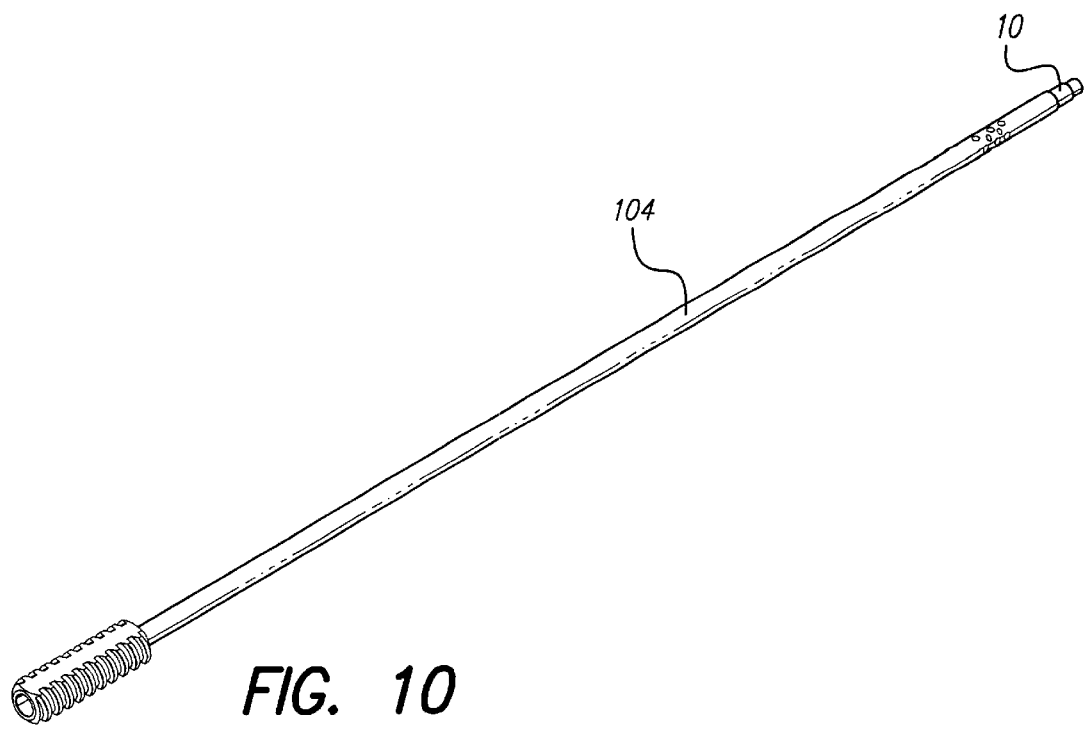
FIG. 10 is a perspective view of the implant holder of FIG. 5A with a BION implant of FIG. 1 in place at the distal end of the implant holder.

In a preferred embodiment, implant holder 100 is packaged and provided with BION implant 10 positioned at the distal end of holder tube 104, as shown in FIG. 10. Packaging and providing the implant already positioned within the tool eases handling and protects the implant. Furthermore, in conjunction with the BION device, this packaging practice also ensures that the BION stimulator is the correct distance into tube 104 and in the correct orientation for its electrical polarity. For instance, the BION microstimulator is inserted in the distal end of tube 104 so that the indifferent electrode lies next to but does not occlude holes 106. Holes 106 allow interstitial fluid to contact the indifferent electrode during implantation. The position of the BION stimulator as provided in tube 104 thus identifies the electrical polarity of the BION stimulator and helps ensure correct implant orientation.

Figure 11:
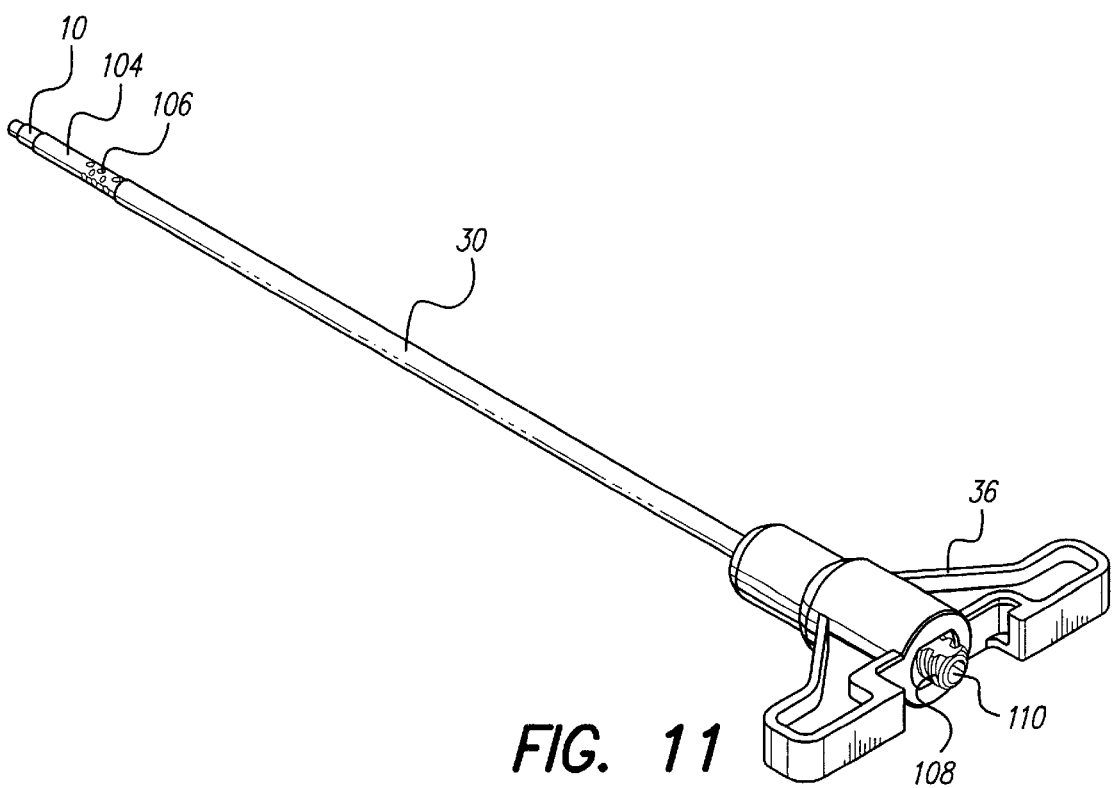
FIG. 11 is a perspective view of the implant holder of FIG. 5A with a BION implant of FIG. 1 inserted, secured to the handle of the tool of the present invention.

Continuing now with the implantation procedure, holder tube 104 containing BION microstimulator 10 is insert into cannula 30, as shown in FIG. 11. This positions the BION device at the previously determined location of lowest sensory threshold. To verify that the BION implant operates at this location, the BION stimulator is externally activated (e.g., with an external radio frequency (RF) coil) and commanded to stimulate with the same settings as were used with the stimulating probe.

If the location requires unacceptable stimulation parameters or if the patient fails to sense stimulation, handle 36 is used to maneuver the BION stimulator (still within holder tube 104 which in turn is within cannula 30) to an acceptable location. If an acceptable location is not found, holder 100 (still containing the BION implant) may be withdrawn from cannula 30. A 24-gauge needle electrode attached to a commercial neurostimulator may then be inserted into cannula 30 and used to determine an alternative location.

Once an acceptable site is found for implant 10 (which is again within implant holder 100 which in turn is held in cannula 30), rod 134 of push rod assembly 130 is inserted into passage 110 of holder tube 104 of implant holder 100 (FIG. 12). Alternatively, the push rod assembly may be in place earlier. If made of preferably non-metal materials (to reduce signal interference), the push rod assembly may be in place during external stimulation of the BION microstimulator.

If necessary, driving wheel 142 is slid distally until the female threads within wheel insert section 144 engage the double lead thread on holder head 108. As wheel knob section 143 of driving wheel 142 is rotated clockwise, the female threads along the inside surface of wheel insert section 144 further engage the double lead thread on holder head 108. Thus, as wheel knob section 143 is turned clockwise, holder tube 104 is drawn proximally as holder head 108 is drawn into wheel insert section 144. As holder tube 104 is drawn proximally into cannula 30, the distal end of rod 134, which is contacting the proximal end of the implant, prevents the implant from also being drawn proximally. Driving wheel 142 is rotated clockwise until enough of holder head 108 is pulled up into wheel insert section 144 to cause implant holder tube 104 to be pulled proximally from around the implant (FIG. 13). Preferably, the release of the implant from holder tube 104 coincides with (or at least precedes) contact between the proximal end of holder head 108 and a distal surface of cap insert section 141, which contact prevents further rotation of driving wheel 142. In this manner, the position of the BION stimulator is rigidly maintained while the tool is disengaged from the implant. Finally, cannula 30 (containing implant holder 100 and push rod assembly 130) is removed through the skin.

As mentioned earlier, it is preferred that as many of the tool components as possible be reusable. In one embodiment, the implant is packaged and provided in the implant holder, so in this case this component would not be reusable. For use with other implantable devices and with medications, however, this packaging arrangement may not be necessary or desired. Therefore, in some cases the implant holder may be reusable, along with the other tool components. In other embodiments, it may be preferable for safety reasons, for instance, that all or most of the tool components be disposable.

As mentioned above, the previous description is of the best mode presently contemplated for carrying out the invention. Upon reviewing the drawings and text herein, alternative configurations of the tool will be apparent to those of skill in the art. For instance, although the above description detailed one configuration and use of the tool tailored for a miniature implantable stimulator (i.e., a BION microstimulator), the tool may be modified in various ways for use with other implantable devices and for implanting medications.

Alternative configurations of the stimulating probe are possible. For instance, the probe may have a hollow insulating body with a metal tip. If the stimulating feature is desired, the tip of the probe may simply be attached to a wire that extends through the probe body, and an indifferent electrode may simply be a small conductor attached to the insulating body an appropriate distance from the tip, with a wire that extends up through the body.

For inserting BION microstimulators or other implants, locating components of the tool may be used to detect and/or confirm proper implant location (see FIG. 14). For instance, rather than using the stimulating probe to determine a proper implant site, the site may be previously identified, and the stimulating probe may facilitate confirmation of the site. Alternatively, the BION implant within the implant holder may be used to confirm the location.

In other embodiments, the probe or other tool component with a blunt tip is used to dissect the approach to the implant area. Then a locating component of the tool is used to identify (i.e., detect) the correct implant location (FIG. 14). For instance, the component may find the location under direct vision, as in endoscopy. The implant site may then be confirmed with, for instance, stimulation via the stimulating probe or preferably with the BION microstimulator in the holder. However, if the implant location is pre-identified, a locating component of the tool may be used simply to confirm the proper implant site. Therefore, a locating component of the tool is defined as a device or means used to determine or to confirm proper implant location. Similarly, locating an implant site comprises determining and/or confirming the proper implant location.

Other implant holder designs are also possible, and can be tailored to the device or medication being implanted. Rather than supplying holes in the holder tube, slots may be used, which may or may not extend all the way to the distal end. Also, for many implants, there is no need for holes or slots in the holder tube.

Other methods of releasing the implant will be apparent to those of skill in the art. For instance, bumps on the surface of the implant tube may fit into holes or indentations in the cannula, so that moving the cannula in a proximal direction also draws the implant tube from around the implant. In this case, it is preferred that a push rod remain in position while the cannula moves. Other methods of securing the implant holder tube and cannula are possible, such as an implant holder head and cannula handle that are keyed, or have mating configurations, as in the primary embodiment.

As previously stated, other implant holder head configurations are possible. In addition, other push rod assembly configurations are conceivable. For instance, rather than separate components that make up the housing, driving wheel and cap, these may instead be formed as one handle. In conjunction with the preferred embodiment, the resulting handle would then have an opening at the distal end, with a female thread to match the male threads on the implant holder. In this case, the push rod would preferably extend distally from the handle through the center of the opening. To engage the implant holder head, the push rod handle would be placed over the proximal end of the implant holder head. As the push rod handle is then turned, the female threads in the push rod handle engage the male threads on the implant holder head. Thus, the implant holder is pulled proximally while the push rod keeps the implant in place.

By rotating the push rod handle (or the driving wheel of the primary embodiment) to make the implant holder retreat, the likelihood of pulling the entire tool, and thus the still contained implant, in a proximal direction, is reduced because the rotating action directs the force perpendicular to the axis of the implant. However, in a further embodiment, rather than a screw, the implant holder head has tabs that protrude through slots in the handle and through slots in the push rod assembly housing. Once the implant is in position, the tabs are pulled in a proximal direction. During this process, the thumb of the hand activating the tabs is preferably positioned at the proximal end of the rod cap, to oppose the pulling force exerted on the tabs. While the tabs slide proximally in the push rod assembly housing slots, the holder tube retracts from around the implant. As in the primary embodiment, the push rod allows the implant to maintain its proper position. Rather than tabs, the tool may be activated with a lever and fulcrum or other suitable mechanism that preferably allows the applied forces to oppose each other.

In another alternative, the cannula also acts as the implant holder. In this case, the handle is preferably modified to additionally perform the function previously performed by the implant holder head, and the distal end of the cannula is modified to be able to securely hold an implant. In operation, the trocar and stimulating probe are inserted and operated essentially as previously described. Then, the implant is placed in the cannula, and pushed distally by inserting the push rod into the cannula after the implant. (In the case of a BION stimulator and similar devices, the implant must be inserted in the correct orientation.) When the push rod is fully inserted into the cannula, the distal end of the rod has pushed the implant into position at the end of the cannula. In the case of a BION stimulator, the implant is now tested by simulating with an external device, such as an RF coil. (Therefore, the distal end of the cannula preferably has holes or slots for implants such as the BION device, just as the implant holder tube of the primary embodiment.) Once the implant is in position, the cannula is retracted from around the implant via mechanisms in the handle and in the push rod housing. For instance, the handle may have female threads that mate with a male double lead thread in the push rod housing. As a wheel or similar mechanism on the housing is turned, the handle and cannula are drawn up to the push rod housing, and the rod remains stationary to ensure the implant remains in the proper position.

In conjunction with the previous alternative, it is also preferable that an implant such as the BION microstimulator be packaged and provided in a manner that identifies the electrical polarity and ensures proper insertion orientation. It is further preferable that this packaging component also be a component of tool. Thus, a BION delivery device is preferably configured to fit only one way into the handle of the cannula, so that the implant is in the proper orientation. The push rod assembly is then inserted, and the rod pushes the insert into place at the distal end of the cannula. In this case, the delivery device has a mechanism, such as female threads, that allow the push rod housing to pull the cannula from the implant with a mating male thread, for instance. Again, the stationary rod ensures the implant is deposited in the preferred location during the retraction of the cannula.

Thus, the invention provides a single, easy to use tool that is used to determine a target location for an implant, and is also used to deliver the implant to the target location. The tool of the present invention also provides components for testing target locations for proper response to electrical stimulation, and for positioning and testing a miniature implantable BION stimulator before depositing the implant precisely at the target location. By using this one tool, surgery time, the number and size of incisions, risk of infection, and likelihood of error are reduced. The tool is preferably ergonomic and light-weight and may be sterilized using standard methods. Most preferably, all components of the tool are able to withstand autoclave sterilization.

While the invention herein disclosed has been described by means of specific embodiments and applications thereof, numerous modifications and variations could be made thereto by those skilled in the art without departing from the scope of the invention set forth in the claims. For instance, the tool may also be used to implant other devices or to implant medications, in addition to miniature neurostimulators. For example, the tool may be used to deliver a chemotherapy treatment. As mentioned above, alternative configurations of the tool may be appropriate depending on the implant item (FIG. 14). In conjunction with implanting a chemotherapy treatment, it may be preferable to use a small diameter endoscope rather than a stimulating probe. The tool component used to locate the proper implant site would then preferably comprise a fiber optic light source and an endoscope in communication with an external monitor.

Other methods and tool components may be used to locate the proper implant site, as illustrated in FIG. 14. For instance, an ultrasound probe may be used to detect motion. Alternatively, a chemical sensor may be used in place of the stimulating probe. The sensor may detect a particular substance, or the sensor may utilize antibodies with a detectable response when they bind an antigen. In yet another embodiment, a temperature sensor may be used in place of the stimulating probe. In this case, a hot or cold substance may be introduced, and the thermal response measured. Additional alternative uses and configurations will be apparent to those skilled in the art from reading the specification and reviewing the drawings herein, without deviating from the spirit of the instant invention.

What is claimed is:

1. A surgical system for inserting an implant comprising:
    an implant;
    a cannula;
    a handle attached to the cannula;
    at least one locating device removably insertable into the cannula;
    an implant holder removably insertable into the cannula; and
    a push rod removably insertable into the implant holder;
    wherein the implant is held by the implant holder; and
    wherein the push rod engages the implant, thereby keeping the implant in place as the implant holder is disengaged from the implant; and
    wherein the implant is a miniature implantable stimulator.

2. The surgical tool according to claim 1 wherein the at least one locating device comprises one or more of a stimulating probe, an endoscope, an ultrasound probe, and the implant.

3. The surgical tool according to claim 1 wherein the implant holder is a Teflon® tube.

4. The surgical tool according to claim 1 wherein the implant holder is configured to retract the implant.

5. The surgical tool according to claim 1 wherein the proximal end of the implant holder comprises a male thread and wherein the proximal end of the push rod comprises a female thread, whereby the implant holder is disengaged from the implant as the male thread of the implant holder engages the female thread of the push rod.

6. The surgical tool according to claim 1 wherein the implant holder is configured to allow external activation of the stimulator.

7. The surgical tool according to claim 6 wherein the stimulator is packaged and provided in the implant holder.

8. A surgical system including an implant and a tool for inserting the implant within a body, the surgical tool comprising means for holding the implant, means for locating a proper implant site and means for depositing the implant at the proper implant site, wherein the means for locating the proper implant site comprises at least means for confirming the proper implant site and wherein the implant is a miniature implantable stimulator.

9. The surgical tool according to claim 8 wherein the means for locating the proper implant site comprises at least one of a stimulating probe component and an endoscope.

10. The surgical tool according to claim 8 further comprising means for externally activating the stimulator.

11. The surgical tool according to claim 8 further comprising means for disengaging from the implant, thereby leaving the implant in the proper implant location.

12. A method of using a surgical tool for implanting a medical device or medication comprising:
    providing a passage through the skin of a body;
    inserting a locating device into a cannula, the cannula including a handle;
    maneuvering the locating device and the cannula to a location considered suitable as an implant site;
    removing the locating device from the cannula;
    inserting an implant holder and an implant into the cannula;
    inserting a push rod into the implant holder until the push rod engages the implant;
    disengaging the implant holder from the implant while using the push rod to keep the implant in place; and
    removing the cannula, the implant holder and the push rod from the body;
    wherein the implant is a miniature implantable stimulator.

13. The method of claim 12 wherein maneuvering the locating device comprises using the locating device to facilitate determining the proper stimulator location.

14. The method of claim 13 wherein the locating device comprises a stimulating probe, and maneuvering the locating device comprises using the stimulating probe to facilitate determining the proper stimulator location.

15. The method of claim 13 further comprising confirming proper implant operation prior to disengaging the implant holder from the implant.

16. The method of claim 15 wherein confirming proper implant operation comprises activating the stimulator.

17. The method of claim 12 further comprising confirming proper implant position prior to disengaging the implant holder from the implant.

18. The method of claim 12 further comprising removing the implant holder containing the implant from the cannula and repeating maneuvering the locating device to facilitate determining an alternative location for the implant.

19. A surgical system comprising:
    an implant; and
    a tool, the tool including;
        means for locating a proper implant site;
        means for positioning the implant at the located site; and
        means for stabilizing the implant during removal of the tool from around the implant;
    wherein the implant is a miniature implantable stimulator.

20. The surgical tool of claim 19 wherein the locating means comprises a means for determining the proper implant site and a means for confirming the proper implant site.

21. The surgical tool of claim 20 wherein the determining means and the confirming means comprise one tool component.

22. The surgical tool of claim 20 wherein the determining means and the confirming means comprise more than one tool component.

23. The surgical tool of claim 22 wherein the confirming means comprises the implant.

24. The surgical tool of claim 19, further comprising:
    a cannula; and
    a handle attached to the cannula;
    wherein the locating means is removably insertable into the cannula.

25. The surgical tool of claim 24 wherein the cannula comprises the positioning means.

26. The surgical tool of claim 24 wherein an implant holder removably insertable into the cannula comprises the positioning means.

27. The surgical tool of claim 24 further comprising a trocar removably insertable into the cannula.

28. The surgical tool of claim 24 wherein the stabilizing means is removably insertable into the cannula.

29. The surgical tool of claim 28 wherein the stabilizing means comprises a push rod.

30. The surgical tool of claim 19 wherein the locating means comprises one or more of a stimulating probe, an endoscope, an ultrasound probe, a temperature probe, and a chemical sensor.

31. The surgical tool of claim 19 wherein the implant is packaged and provided in the implant positioning means.

32. The surgical tool of claim 19 wherein the positioning means further comprises means for retracting the implant.

* * * * *